(12) United States Patent
Hynes et al.

(10) Patent No.: US 10,172,650 B2
(45) Date of Patent: *Jan. 8, 2019

(54) SPINAL IMPLANT SYSTEM AND METHOD

(71) Applicant: Warsaw Orthopedic, Inc., Warsaw, IN (US)

(72) Inventors: Richard A. Hynes, Melbourne Beach, FL (US); Alan Rezach, Atoka, TN (US); Rodney R Ballard, Lakeland, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 976 days.

This patent is subject to a terminal disclaimer.

(21) Appl. No.: 14/520,100

(22) Filed: Oct. 21, 2014

(65) Prior Publication Data

US 2016/0106479 A1 Apr. 21, 2016

(51) Int. Cl.
*A61B 17/80* (2006.01)
*A61B 17/70* (2006.01)
*A61B 17/17* (2006.01)
*A61B 17/86* (2006.01)
*A61B 17/88* (2006.01)

(52) U.S. Cl.
CPC ...... *A61B 17/7059* (2013.01); *A61B 17/1757* (2013.01); *A61B 17/7037* (2013.01); *A61B 17/7044* (2013.01); *A61B 17/7055* (2013.01); *A61B 17/808* (2013.01); *A61B 17/862* (2013.01); *A61B 17/8615* (2013.01); *A61B 17/888* (2013.01); *A61B 17/8891* (2013.01)

(58) Field of Classification Search
CPC ............ A61B 17/7001; A61B 17/7044; A61B 17/7035; A61B 17/7055; A61B 17/7059
See application file for complete search history.

(56) References Cited

U.S. PATENT DOCUMENTS

2013/0085534 A1* 4/2013 Hainard ............. A61B 17/7055
606/278

* cited by examiner

*Primary Examiner* — Si Ming Ku

(57) ABSTRACT

A spinal implant system comprises a plate including a surface that defines a first cavity and a second cavity. The first cavity is oriented to implant a multi-axial fastener with a sacrum. The second cavity is oriented to implant a fastener with an ala of a sacrum. A surgical instrument is engageable with the plate. At least one of the plate and the surgical instrument includes an engagement surface for connection therebetween. Systems and methods of use are disclosed.

22 Claims, 18 Drawing Sheets

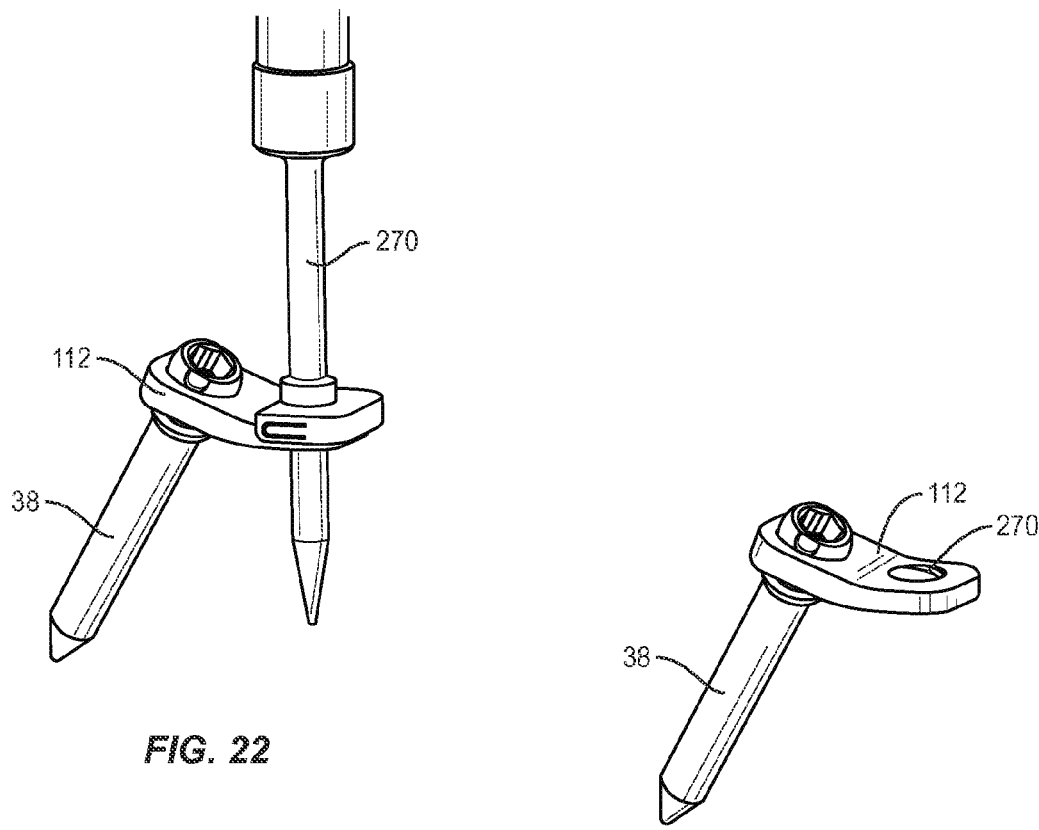
FIG. 22
FIG. 23
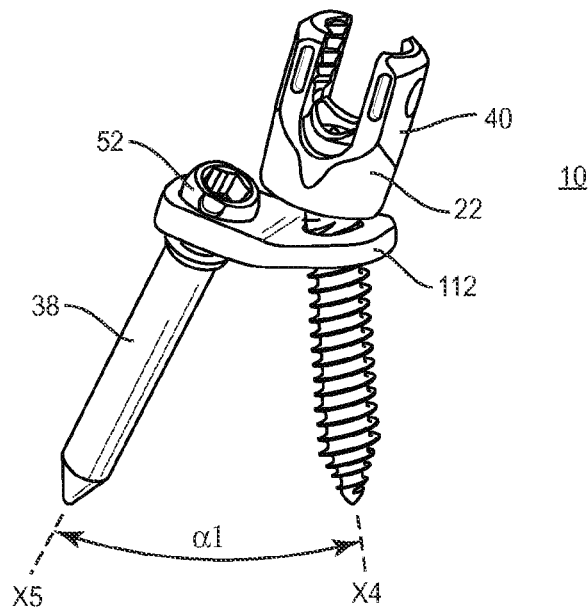
FIG. 24

SPINAL IMPLANT SYSTEM AND METHOD

TECHNICAL FIELD

The present disclosure generally relates to medical devices for the treatment of musculoskeletal disorders, and more particularly to a surgical system for implant delivery to a surgical site and a method for treating a spine.

BACKGROUND

Spinal pathologies and disorders such as scoliosis and other curvature abnormalities, kyphosis, degenerative disc disease, disc herniation, osteoporosis, spondylolisthesis, stenosis, tumor, and fracture may result from factors including trauma, disease and degenerative conditions caused by injury and aging. Spinal disorders typically result in symptoms including deformity, pain, nerve damage, and partial or complete loss of mobility.

Non-surgical treatments, such as medication, rehabilitation and exercise can be effective, however, may fail to relieve the symptoms associated with these disorders. Surgical treatment of these spinal disorders includes fusion, fixation, correction, discectomy, laminectomy and implantable prosthetics. As part of these surgical treatments, spinal constructs, such as, for example, bone fasteners, spinal rods and interbody devices can be used to provide stability to a treated region. For example, during surgical treatment, surgical instruments can be used to deliver components of the spinal constructs to the surgical site for fixation with bone to immobilize a joint. Fasteners may also be attached to iliac bone. This disclosure describes an improvement over these prior art technologies.

SUMMARY

In one embodiment, a spinal implant system is provided. The spinal implant system comprises a plate including a surface that defines a first cavity and a second cavity. The first cavity is oriented to implant a multi-axial fastener with a sacrum. The second cavity is oriented to implant a fastener with an ala of a sacrum. A surgical instrument is engageable with the plate. At least one of the plate and the surgical instrument includes an engagement surface for connection therebetween. Systems and methods of use are disclosed.

BRIEF DESCRIPTION OF THE DRAWINGS

The present disclosure will become more readily apparent from the specific description accompanied by the following drawings, in which:

FIG. 22 is a break away view of components of one embodiment of a system in accordance with the principles of the present disclosure;

FIG. 23 is a perspective view of components of one embodiment of a system in accordance with the principles of the present disclosure;

FIG. 24 is a perspective view of components of one embodiment of a system in accordance with the principles of the present disclosure;

DETAILED DESCRIPTION

Figure 1:
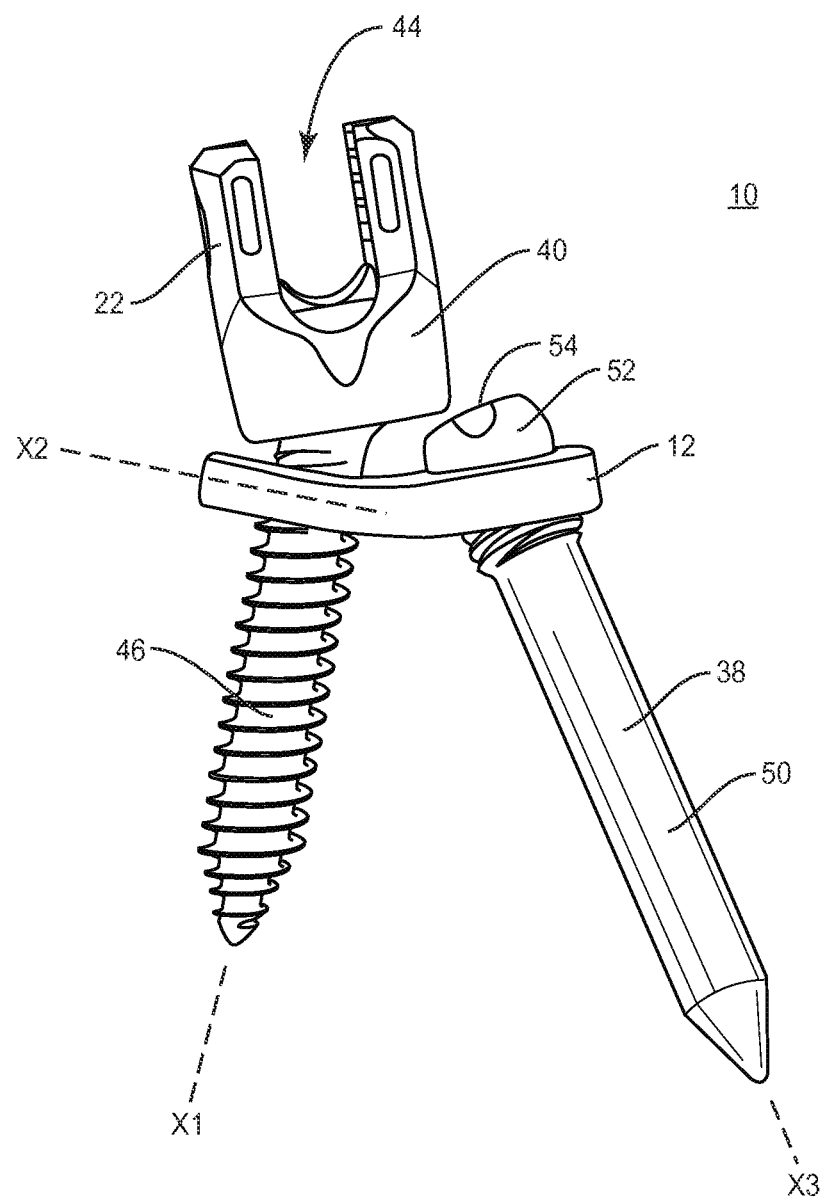
FIG. 1 is a side view of components of one embodiment of a system in accordance with the principles of the present disclosure.

The exemplary embodiments of the surgical system and related methods of use disclosed are discussed in terms of medical devices for the treatment of musculoskeletal disorders and more particularly, in terms of a surgical system for implant delivery to a surgical site and a method for treating a spine. In one embodiment, the systems and methods of the present disclosure are employed with a spinal joint and fusion, for example, with a cervical, thoracic, lumbar and/or sacral region of a spine. In one embodiment, the systems and methods can be employed with a spinal fusion, such as, for example, a midline posterior joint fusion.

In one embodiment, the present system includes an implant, such as, for example, a plate configured for engagement with two screws. In some embodiments, the system includes a dual screw sacral plate configured for use with a midline pedicle screw approach. In one embodiment, the system includes a screw that is configured for alignment with a sacral trajectory and/or surgical pathway and a screw that is configured for alignment with a sacral alar trajectory and/or surgical pathway. In one embodiment, the system includes a plate that is configured for positioning on a left side or a right side of a patient's body. In one embodiment, the system includes a kit comprising one or more alar screws that are provided with various lengths, such as, for example, 30 millimeters (mm), 35 mm, 40 mm, 45 mm and/or 50 mm. In one embodiment, the system includes a surgical instrument, such as, for example, an awl that is connected with a plate for insertion adjacent a surgical site along an S1 trajectory and/or surgical pathway. In one embodiment, the system includes a surgical instrument, such as, for example, an awl that guides an alar screw along an alar trajectory and/or surgical pathway. In some embodiments, the same awls can be utilized for left oriented plates or right oriented plates.

In one embodiment, the system includes a surgical instrument, such as, for example, an awl guide. In one embodiment, the awl guide is utilized to target an S1 vertebra and ensure an alar trajectory is based upon the S1 vertebra positioning. In one embodiment, the present system is employed with a method such that use of the awl guide requires one set of guides (Left/Right) for all sizes of plates. In one embodiment, the awl guide provides a rigid interface between an S1 vertebra awl and nail trajectory.

In one embodiment, the present system includes an implant, such as, for example, an alar nail that is threaded with a plate on a back table and employed with a method comprising the step of determining a length of the alar nail. In some embodiments, this step facilitates placement of the alar nail. In one embodiment, the awl guide is identical to the plate for alignment of implants along selected trajectories. In some embodiments, the system includes a surgical instrument, such as, for example, a driver including spring tabs and employed with a method comprising the step of connecting the driver with the alar nail for insertion along an alar trajectory. In some embodiments, the method includes the step of removing the awl guide. In some embodiments, the method includes the step of, after insertion of the alar nail, aligning the plate with the original S1 awl pilot hole for engagement of a multi-axial bone screw (MAS). In some embodiments, the present system and method reduce cross threading and facilitate proper alignment of awl trajectories.

In one embodiment, the method includes the step of positioning a plate about an S1 vertebra awl and a bone fastener is inserted through the plate. In one embodiment, the method includes the step of snapping a plate onto an awl guide holder. In one embodiment, the method includes the step of attaching the awl guide holder with the plate and placing the components in a desired position on a sacrum and the awl is malleted in place. In one embodiment, the method includes the step of placing a sacral nail screw through the awl guide holder and/or loaded in the awl guide holder and is malleted in place, except for the remaining 3-5 mm of a pilot hole. In one embodiment, the method includes the step of screwing a fastener in the final 3-5 mm of the pilot hole and screwed in with threads on a nose and a neck of the nail screw.

In one embodiment, the method includes the step of removing the awl guide holder and leaving the nail screw in a selected position. In one embodiment, the method includes the step of providing a bone fastener with a preloaded nub, which is screwed into a plate and locking the nub into the plate and resisting potential back out of the nail screw from a cavity and into an ala of a sacrum. In one embodiment, the method includes pulling out an awl from a first cavity of a plate and driving a MAS into a pilot hole established by the awl.

In one embodiment, a bone fastener comprises a nail having a spherical head and a bone fastener comprising a MAS. In one embodiment, the system comprises a plate cover or a layer configured to lock a spherical head of a nail in position. In one embodiment, a bone fastener is received in a first cavity of the plate to engage an S1 vertebra. In one embodiment, a bone fastener is received in a second cavity of a plate to engage an ala of a sacrum.

In one embodiment, the system is employed with a method for implanting components of the system with vertebrae of a patient. In one embodiment, the method includes the step of threading an awl through a first cavity of a plate and into an S1 vertebra to stabilize the plate and establish a desired trajectory. In one embodiment, the method includes the step of driving an alar nail through a cavity of a plate and into an ala of a sacrum. In one embodiment, the method includes the step of drawing out an awl from a cavity of a plate. In one embodiment, the method includes the step of positioning a plate cover over the plate to lock an alar nail in a selected position. In one embodiment, the method includes the step of threading an insert into a cavity of a plate and passing a MAS through a cavity of the plate and driving the MAS into a pilot hole established by an awl.

In one embodiment, the system includes a plate for engagement with a sacrum having a low profile. In one embodiment, the system is employed with a method that includes the step of threading an awl through a cavity of a plate and into an S1 vertebra to stabilize the plate and establish a desired trajectory. In one embodiment, the method includes the step of driving an alar nail through a cavity of a plate and into an ala of a sacrum. In one embodiment, the alar nail comprises proximal threads to engage threads on an inner surface of a cavity of the plate. In one embodiment, the method includes the step of removing the awl from a cavity of a plate. In one embodiment, the method includes the step of threading an insert into a cavity of a plate and passing a MAS through the cavity and driving the MAS into a pilot hole established by the awl.

In one embodiment, the system includes a plate attachable to vertebrae in a medial-lateral orientation. In one embodiment, the system includes a plate positioned above an S1 foramen during a surgical procedure. In one embodiment, the plate is configured for disposal of a MAS and a sacral alar bone screw. In one embodiment, the MAS includes a receiver that can be oriented to prevent the bone screw from backing out of an S1 vertebra. In some embodiments, the angles of the bone screws may be selectively adjusted. In some embodiments, an interface between a plate and the MAS facilitates a tight fit to prevent the MAS from backing out of the plate and/or tissue. In one embodiment, the MAS interlocks into a plate such that resistance from being pulled out and/or backing out is increased.

In one embodiment, the system includes a plate configured for attachment to a sacrum and is symmetrically configured such that it may be disposed on either side of the sacrum of the patient's body. In one embodiment, the plate is asymmetric and comprises a left version and a right version. In one embodiment, a bone fastener comprises a headless bone screw having a diameter of 6.5 mm, 7.5 mm or 8.5 mm. In one embodiment, the bone fastener comprises a 4 mm dual lead thread. In one embodiment, the bone fastener is attached to an S1 vertebra at an angular orientation of 25 degrees in a medial direction and/or 25 degrees in a lateral direction.

In one embodiment, the system includes inserts configured to be positioned in a first cavity and/or a second cavity of a plate. In one embodiment, an insert includes an outer thread configured to facilitate engagement with a cavity. In one embodiment, the insert includes an inner thread configured to facilitate engagement with a bone screw.

In one embodiment, the present system is employed with a method for implanting components of the system with one or more vertebra of a patient. In one embodiment, the system includes an insert configured to receive a bone fastener and the method includes the step of inserting the bone fastener into a plate. In one embodiment, the method includes the step of inserting an awl through a first cavity of a plate and into an S1 vertebra to stabilize the plate and establish a desired trajectory. In one embodiment, the awl locks into the plate to resist being pulled out and/or backing out axially. In some embodiments, the insert may be sized to accommodate use of a variety of MAS sizes. In one embodiment, the inserts may be color coded. In one embodiment, the insert is configured to apply downward pressure on the plate cover to lock the spherical head of the alar nail in place.

In some embodiments, the present system and/or method are used with surgical navigation, such as, for example, fluoroscope or image guidance. In some embodiments, the presently disclosed system and/or method reduce operating time for a surgical procedure and reduce radiation exposure due to fluoroscope or image guidance, for example, by eliminating procedural steps and patient repositioning by implanting system components in one body position.

In one embodiment, one or all of the components of the surgical system are disposable, peel-pack or pre-packed sterile devices. One or all of the components of the surgical system may be reusable. The surgical system may be configured as a kit with multiple sized and configured components.

The present disclosure may be understood more readily by reference to the following detailed description of the embodiments taken in connection with the accompanying drawing figures, which form a part of this disclosure. It is to be understood that this application is not limited to the specific devices, methods, conditions or parameters described and/or shown herein, and that the terminology used herein is for the purpose of describing particular embodiments by way of example only and is not intended to be limiting. Also, in some embodiments, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior".

As used in the specification and including the appended claims, "treating" or "treatment" of a disease or condition refers to performing a procedure that may include administering one or more drugs to a patient (human, normal or otherwise or other mammal), employing implantable devices, and/or employing instruments that treat the disease, such as, for example, micro discectomy instruments used to remove portions bulging or herniated discs and/or bone spurs, in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. Also, as used in the specification and including the appended claims, the term "tissue" includes soft tissue, muscle, ligaments, tendons, cartilage and/or bone unless specifically referred to otherwise.

The following discussion includes a description of a surgical system including a surgical instrument, one or more implants, related components and methods of employing the surgical system. Alternate embodiments are also disclosed. Reference is made in detail to the exemplary embodiments of the present disclosure, which are illustrated in the accompanying figures. Turning to FIGS. 1-9, there are illustrated components of a spinal implant system 10.

The components of spinal implant system 10 can be fabricated from biologically acceptable materials suitable for medical applications, including metals, synthetic polymers, ceramics and bone material and/or their composites. For example, the components of spinal implant system 10, individually or collectively, can be fabricated from materials such as stainless steel alloys, aluminum, commercially pure titanium, titanium alloys, Grade 5 titanium, super-elastic titanium alloys, cobalt-chrome alloys, stainless steel alloys, superelastic metallic alloys (e.g., Nitinol, super elasto-plastic metals, such as GUM METAL® manufactured by Toyota Material Incorporated of Japan), ceramics and composites thereof such as calcium phosphate (e.g., SKELITE™ manufactured by Biologix Inc.), thermoplastics such as polyaryletherketone (PAEK) including polyetheretherketone (PEEK), polyetherketoneketone (PEKK) and polyetherketone (PEK), carbon-PEEK composites, PEEK-BaSO$_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate, tri-calcium phosphate (TCP), hydroxyapatite (HA)-TCP, calcium sulfate, or other resorbable polymers such as polyaetide, polyglycolide, polytyrosine carbonate, polycaroplaetohe and their combinations.

Various components of spinal implant system 10 may have material composites, including the above materials, to achieve various desired characteristics such as strength, rigidity, elasticity, compliance, biomechanical performance, durability and radiolucency or imaging preference. The components of spinal implant system 10, individually or collectively, may also be fabricated from a heterogeneous material such as a combination of two or more of the above-described materials. The components of spinal implant system 10 may be monolithically formed, integrally connected or include fastening elements and/or instruments, as described herein.

System 10 includes an implant, such as, for example, a plate 12. In one embodiment, plate 12 is configured for disposal in a medial-lateral orientation between a sacrum and a sacral ala. Plate 12 includes a substantially rectangular configuration and defines a longitudinal axis X1. In some embodiments, plate 12 can be variously configured, such as, for example, oval, oblong, triangular, square, polygonal, irregular, uniform, non-uniform, variable, hollow and/or tapered. Plate 12 includes a wall 14 that defines an axis X2 and defines a wall thickness t1. Wall 14 includes an inner surface 16 and an outer surface 18. In one embodiment, axis X2 is disposed in a perpendicular orientation relative to axis X1. In some embodiments, axis X2 may be disposed at various orientations relative to axis X1, such as, for example, transverse, and/or angular orientations, such as acute or obtuse.

Surface 16 defines a cavity, such as, for example, an opening 20. Opening 20 is configured to receive a fastener, such as, for example, a MAS 22. Opening 20 is aligned with axis X1. In some embodiments, opening 20 is aligned with a surgical pathway, approach and/or trajectory, as described herein, to orient MAS 22 for implantation with tissue, such as, for example, an S1 vertebra of a sacrum S, as shown for example in FIGS. 10-13. In some embodiments, opening 20 is aligned with a surgical pathway, approach and/or trajectory that communicates with a posterior mid-line surgical pathway, approach and/or trajectory, as described herein.

Opening 20 includes an engagement surface 24 configured to facilitate engagement with screw 22. In one embodiment, surface 24 is smooth. In one embodiment, surface 24 includes a threaded surface configured to facilitate engagement with a threaded shaft of MAS 22, as described herein.

Surface 18 is configured for engagement with tissue of an S1 vertebra. In some embodiments, surface 18 may include alternate surface configurations, such as, for example, rough, arcuate, undulating, mesh, porous, semi-porous, dimpled and/or textured to facilitate engagement with tissue.

Figure 2:
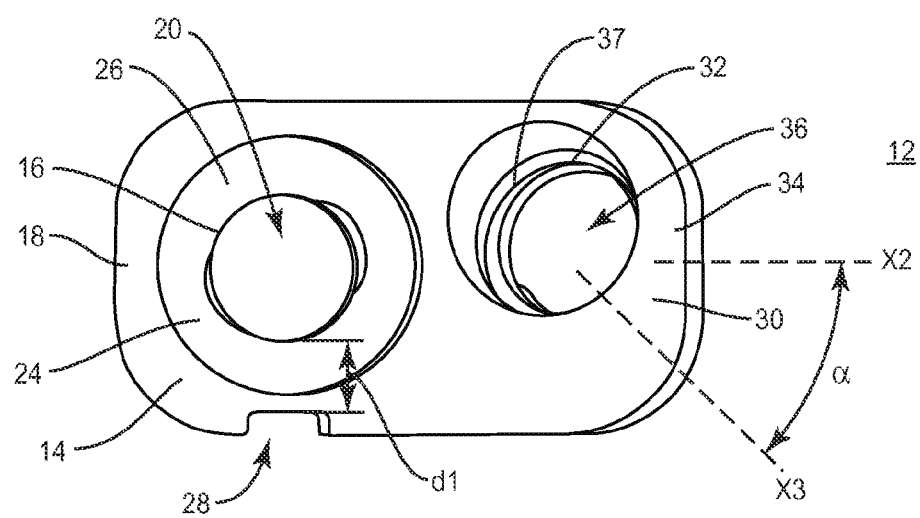
FIG. 2 is a top view of a component of the system shown in FIG. 1.

Surface 18 defines a cavity, such as, for example, a pocket 26 configured for disposal about opening 20. Pocket 26 is configured for disposal with a surgical instrument, such as, for example, an awl 70, as described herein. As shown in FIG. 2, pocket 26 is circular in shape. In some embodiments, all or only a portion of pocket 26 may have alternate configurations, such as, for example, oval, oblong, triangular, square, polygonal, irregular, uniform, non-uniform, offset, staggered, and/or tapered. Pocket 26 includes a wall 27 configured for a nested engagement with awl 70, as described herein.

Surface 18 defines an opening, such as, for example, a recess 28 configured for engagement with awl 70. Recess 28 includes a rectangular cross section. In some embodiments, all or only a portion of recess 28 may have alternate cross section configurations, such as, for example, oval, oblong, triangular, square, polygonal, irregular, uniform, non-uniform, offset, staggered, and/or tapered to facilitate engagement with awl 70. Recess 28 is positioned a distance d1 from wall 27 of pocket 26 to facilitate engagement of awl 70 with opening 20 and forming a friction fit with awl 70. In one embodiment, recess 28 comprises a lateral slot.

Plate 12 includes a wall 30 that defines a wall thickness t2. In one embodiment, thickness t1 is less than thickness t2. In one embodiment, thickness t1 is greater than thickness t2. In one embodiment, thickness t1 is equal to thickness t2. Wall 30 includes an inner surface 32 and an outer surface 34.

Figure 3:
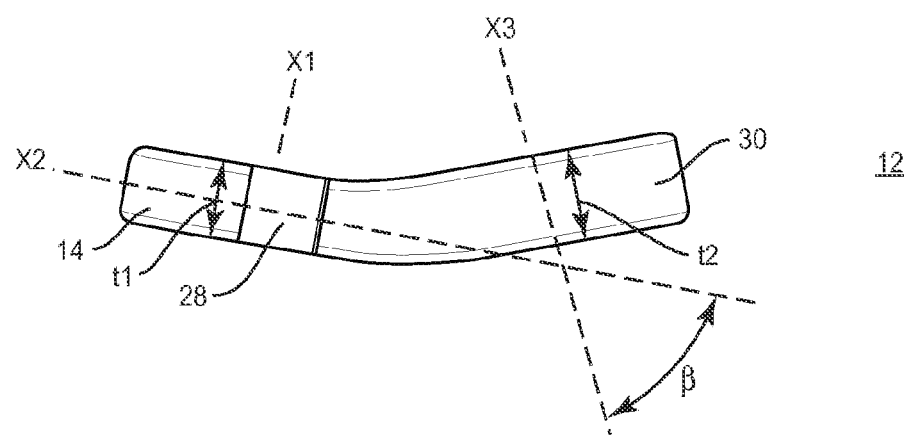
FIG. 3 is a side view of a component of the system shown in FIG. 1.
Figure 4:
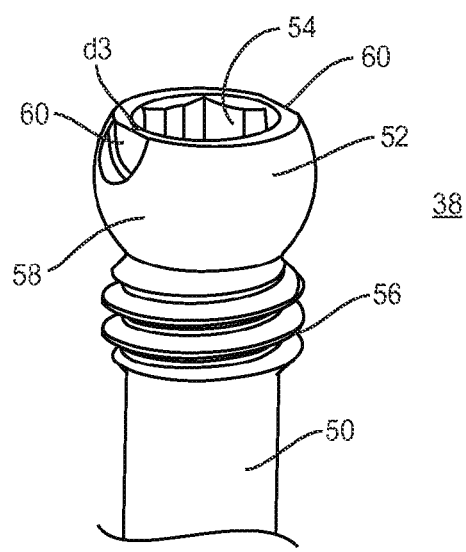
FIG. 4 is a break away view of a component of one embodiment of a system in accordance with the principles of the present disclosure.

Surface 32 defines a cavity, such as, for example, an opening 36. Opening 36 defines an axis X3 and is configured to receive a fastener, such as, for example, a sacral alar nail 38. Axis X3 is offset from axis X2 to facilitate insertion of alar screw 38 with plate 12 and/or tissue. Opening 36 is configured for disposal of alar nail 38 and aligns alar nail 38 with axis X3. As such, the longitudinal axis of alar nail 38 is co-axial with axis X3. In some embodiments, axis X3 is disposed at a compound angle relative to axis X1 and/or axis X2. In some embodiments, axis X3 is disposed at a compound angle relative to axis X2, which includes orientation of axis X3 at an angle α, for example in a lateral direction, relative to axis X2 and at an angle β, for example in a cephalad-caudal direction, relative to axis X2, as shown in FIGS. 1-3. As such, for example, MAS 22 is aligned with axis X1 for implantation with an S1 vertebra and alar nail 38 is aligned with axis X3 for implantation with an alar region of a sacrum to attach plate 12 with a sacrum, as described herein. In some embodiments, axis X3 may be oriented at a single angle relative to axis X1 and/or axis X2. In some embodiments, angle α and/or angle β can include an angle in a range of approximately 0 through 90 degrees. In one embodiment, angle α is approximately 20 degrees in a lateral direction and/or angle β is approximately 45 degrees in a cephalad-caudal direction.

Surface 34 is configured for engagement with tissue of the ala. In some embodiments, surface 34 may include alternate surface configurations, such as, for example, rough, arcuate, undulating, mesh, porous, semi-porous, dimpled and/or textured to facilitate engagement with tissue.

In one embodiment, alar nail 38 has varied lengths, such as, for example, 30 mm, 35 mm, 40 mm, 45 mm or 50 mm and/or system 10 can comprise a kit with such variously sized nails 38. In one embodiment, the fastener is a nail. In one embodiment, the fastener is a curved nail. In some embodiments, opening 36 is oriented to implant alar nail 38 with tissue, such as, for example, an ala of a sacrum. In some embodiments, opening 36 is offset from axis X1. In some embodiments, opening 36 is aligned with a surgical pathway, approach and/or trajectory, as described herein, to orient alar nail 38 for implantation with an alar region of a sacrum. In some embodiments, opening 36 is aligned with a surgical pathway, approach and/or trajectory that communicates with a posterior mid-line surgical pathway, approach and/or trajectory, as described herein.

Opening 36 includes an engagement surface 37 configured to facilitate engagement with alar nail 38. In one embodiment, surface 37 is smooth. In one embodiment, surface 37 includes a threaded surface configured to facilitate engagement with a threaded shaft of alar nail 38, as described herein.

In some embodiments, nail 38 is configured for insertion into an ala region of sacrum, as described herein. Nail 38 includes a shaft 50 having a substantially cylindrical cross-section along its length and a head 52. Shaft 50 includes an outer surface having a smooth surface along a portion of shaft 50 and an external thread form 56 disposed along a portion of shaft 50.

Figure 6:
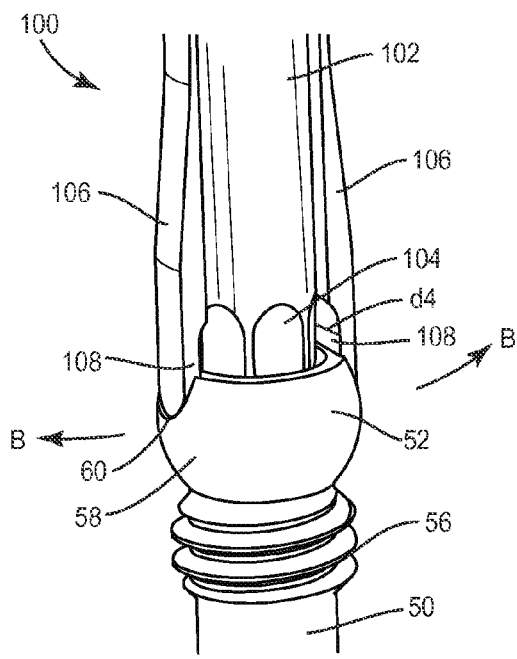
FIG. 6 is a break away view of components of one embodiment of a system in accordance with the principles of the present disclosure.

Head 52 includes a tool engaging portion 54 configured to engage a surgical tool or instrument, as described herein. In one embodiment, portion 54 includes a hexagonal cross-section to facilitate engagement with a surgical tool or instrument, as described herein. In some embodiments, portion 54 may have alternative cross-sections, such as, for example, rectangular, polygonal, hexalobe, oval, or irregular. In some embodiments, as shown in FIG. 6, head 52 includes a surface 58 that defines cavities, such as, for example, recesses 60 configured to receive a surgical instrument, such as, for example, a driver 100. Recesses 60 are disposed about portion 54 a distance d3 from portion 54 to facilitate engagement with driver 100.

In one embodiment, plate 12 includes visual indicia configured to provide configuration and/or a dimension of plate 12. In some embodiments, system 10 may comprise a kit including a plurality of plates with visual indicia indicative of their respective configuration and dimension. In some embodiments, the visual indicia may include color coding to provide configuration and/or a dimension of plate 12. In some embodiments, plate 12 has indicia that displays configuration information for disposal of plate 12 on a right side of a patient or a left side of a patient.

MAS 22 includes a head 40 having a pair of spaced apart arms 42 having an inner surface that defines a U-shaped passageway 44. Passageway 44 is configured for disposal of an implant, such as, for example, a spinal rod (not shown). In some embodiments, all or only a portion of passageway 44 may have alternate cross section configurations, such as, for example, oval, oblong, triangular, square, polygonal, irregular, uniform, non-uniform, offset, staggered, and/or tapered. In some embodiments, arms 42 may be disposed at alternate orientations, relative to the longitudinal axis of MAS 22, such as, for example, transverse, perpendicular and/or other angular orientations such as acute or obtuse, co-axial and/or may be offset or staggered. The inner surface of head 40 includes a thread form configured for engagement with a coupling member, such as, for example, a set screw (not shown). The set screw is threaded with head 40 to attach, fix and/or lock the spinal rod, either provisionally or permanently, with MAS 22 and/or plate 12, as described herein.

MAS 22 includes a shaft 46 configured for penetrating tissue, such as, for example, a sacrum. Shaft 46 has a cylindrical cross-sectional configuration and includes an outer surface having an external thread form. In some embodiments, the external thread form may include a single thread turn or a plurality of discrete threads. In some embodiments, other engaging structures may be located on shaft 46, such as, for example, a nail configuration, barbs, expanding elements, raised elements and/or spikes to facilitate engagement of shaft 46 with tissue.

In some embodiments, all or only a portion of shaft 46 may have alternate cross section configurations, such as, for example, oval, oblong, triangular, square, polygonal, irregular, uniform, non-uniform, offset, staggered, undulating, arcuate, variable and/or tapered. In some embodiments, the outer surface of shaft 46 may include one or a plurality of openings. In some embodiments, all or only a portion of the outer surface of shaft 46 may have alternate surface configurations to enhance fixation with tissue, such as, for example, rough, arcuate, undulating, mesh, porous, semi-porous, dimpled and/or textured. In some embodiments, all or only a portion of shaft 46 may be disposed at alternate orientations, relative to its longitudinal axis, such as, for example, transverse, perpendicular and/or other angular orientations such as acute or obtuse, co-axial and/or may be offset or staggered. In some embodiments, all or only a portion of shaft 46 may be cannulated.

Figure 5:
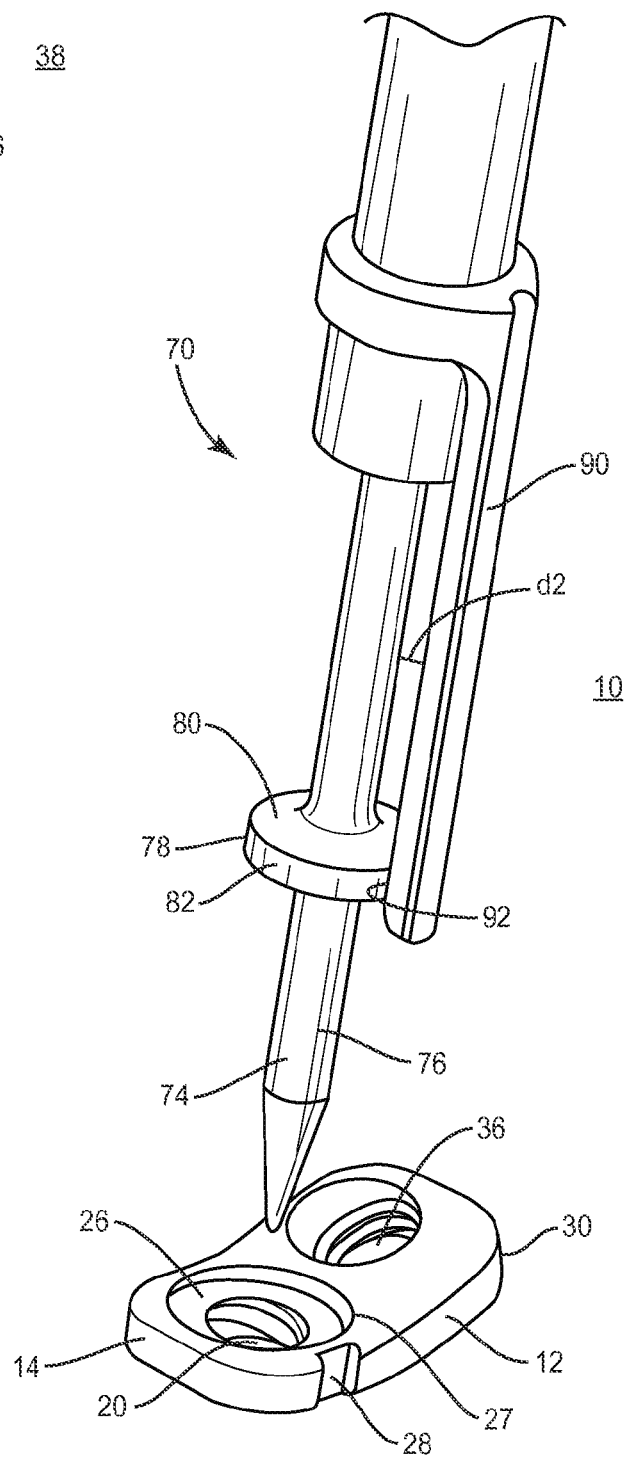
FIG. 5 is a break away view of components of one embodiment of a system in accordance with the principles of the present disclosure.

In some embodiments, system 10 includes a surgical instrument, such as, for example, awl 70, as shown in FIG. 5. Awl 70 includes an end 72 and an end 74. End 74 includes a shaft 76 configured for penetrating tissue. Awl 70 is configured for disposal with opening 20 to provisionally fix placement of plate 12 at the surgical site and/or to form a pilot hole in an S1 vertebra of a sacrum for MAS 22. Awl 70 includes an engagement portion, such as, for example, a disc 78 configured for engagement with pocket 26. Disc 78 includes a surface 80 that defines a wall 82. Wall 82 is configured for nesting engagement with wall 27. In some embodiments, the engagement portion may have alternate cross section configurations, such as, for example, oval, oblong, triangular, square, polygonal, irregular, uniform, non-uniform, offset, staggered, and/or tapered to facilitate engagement with pocket 26.

Awl 70 includes a spring tab, such as, for example, a prong 90 configured for engagement with recess 28. Prong 90 includes a surface 92 and is configured to snap into engagement with recess 28 to form a friction fit between surface 92 and surface 18 to facilitate insertion and/or delivery of plate 12 adjacent to a surgical site, as described herein. Prong 90 is connected with shaft 86 such that prong 90 extends substantially parallel to shaft 86 and a distance d2 from shaft 86.

Distance d2 is less than distance d1 such that as prong 90 translates along surface 18 into recess 28, prong 90 is deflected outward such that the resultant bias forms a friction fit between surface 92 and surface 18. End 72 includes a tool engaging portion 94 configured to engage a surgical tool or instrument, as described herein. In one embodiment, portion 94 includes a hexagonal cross-section to facilitate engagement with a surgical tool or instrument, as described herein.

System 10 includes a surgical instrument, such as, for example, a driver 100, as shown in FIG. 6. Driver 100 includes a shaft 102 including a distal portion 104 having a hexagonal cross-section to facilitate engagement with nail 38. Driver 100 is configured for disposal with nail 38 to deliver and/or position nail 38 with an ala region of a sacrum. Driver 100 includes spring tabs, such as, for example, prongs 106 configured for engagement with recesses 60. Prongs 106 each include a surface 108 configured to deflect, snap and/or bias into engagement with recesses 60 to form a friction fit between surface 108 and surface 58 to facilitate insertion adjacent a surgical site, as described herein. Prongs 106 are connected with shaft 102 such that prongs 106 extend parallel to shaft 102 and a distance d4 from shaft 102. Distance d4 is less than distance d3 such that as prongs 106 translate along surface 58 into indents 60, prongs 106 are deflected outward such that the resultant bias forms a friction fit between surface 108 and surface 58.

In assembly, operation and use, system 10, similar to the systems and methods described herein, is employed with a surgical procedure for treatment of a spinal disorder affecting a section of a spine of a patient, as discussed herein. System 10 is employed with a surgical procedure for treatment of a condition or injury of an affected section of the spine including vertebrae V. In one embodiment, as shown in FIGS. 5-13, the components of system 10 are attached to vertebrae V including sacrum S.

In use, to treat a selected section of vertebrae, a medical practitioner obtains access to a surgical site including vertebrae in any appropriate manner, such as through incision and retraction of tissues. In some embodiments, system 10 can be used in any existing surgical method or technique including open surgery, mini-open surgery, minimally invasive surgery and percutaneous surgical implantation, whereby vertebrae is accessed through a mini-incision, or sleeve that provides a protected passageway to the area. Once access to the surgical site is obtained, the particular surgical procedure can be performed for treating the spine disorder.

An incision is made in the body of a patient and a cutting instrument (not shown) creates a surgical pathway in alignment with a posterior mid-line surgical approach for implantation of components of system 10. A preparation instrument (not shown) can be employed to prepare tissue surfaces of vertebrae, as well as for aspiration and irrigation of a surgical region.

Figure 10:
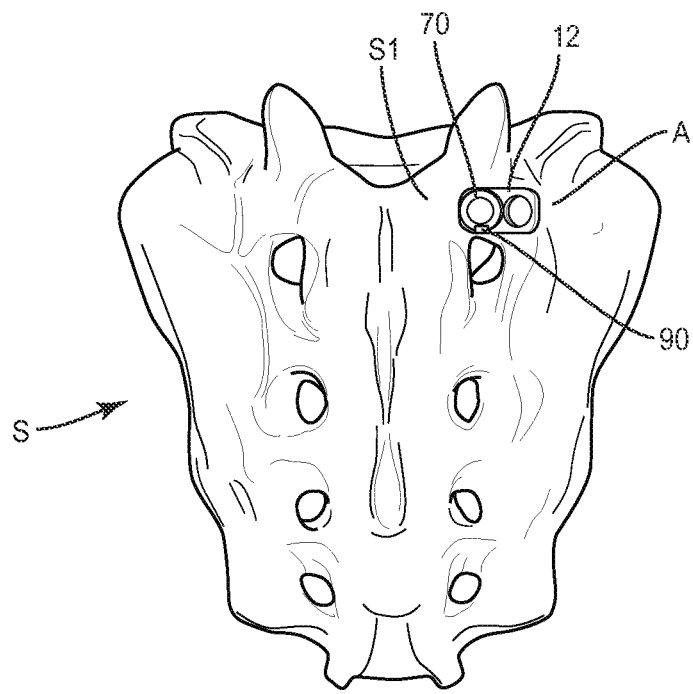
FIG. 10 is a plan view of components of one embodiment of a system in accordance with the principles of the present disclosure disposed with vertebrae.
Figure 11:
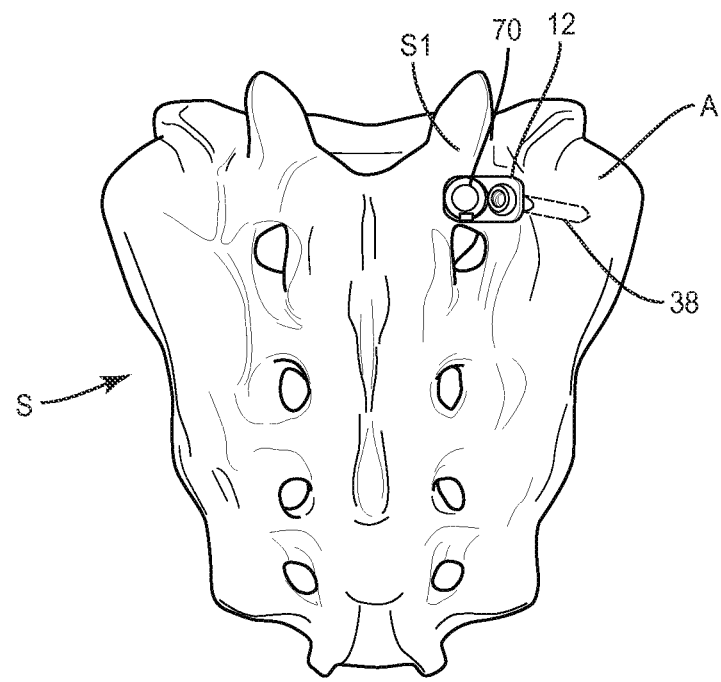
FIG. 11 is a plan view of components of one embodiment of a system in accordance with the principles of the present disclosure disposed with vertebrae.

In some embodiments, system 10 comprises a kit including a plurality of plates 12 of varying configuration and/or dimension. In some embodiments, a plate 12 is selected from the kit for employing with the treatment at the surgical site. As shown in FIG. 5, awl 70 is connected with opening 20 of a selected plate 12. Shaft 74 is passed through opening 20 such that disc 80 is disposed within pocket 26. Wall 82 is nested with wall 27. Prong 90 translates over surface 18 into recess 28 such that prong 90 is deflected outward, as shown by arrow A in FIG. 7. Deflection of prong 90 causes the resultant bias of prong 90 to form a friction fit engagement between surface 92 and surface 18 to releasably fix awl 70 with plate 12. Plate 12 is delivered along the surgical pathway to the surgical site, as shown in FIG. 10. Awl 70 is aligned and engaged with sacrum S along a TS1 trajectory, as shown in FIG. 13, to penetrate tissue of sacrum S and facilitate formation of a pilot hole in an S1 vertebra.

Figure 7:
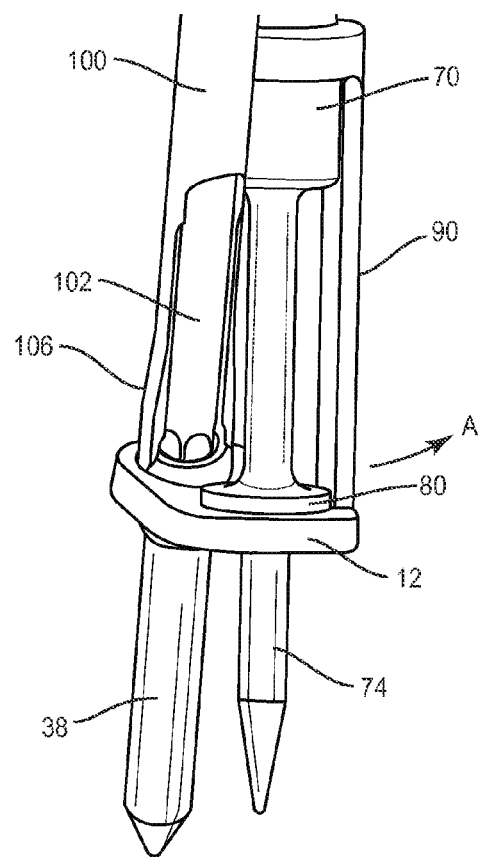
FIG. 7 is a break away view of the components of one embodiment of a system in accordance with the principles of the present disclosure.
Figure 8:
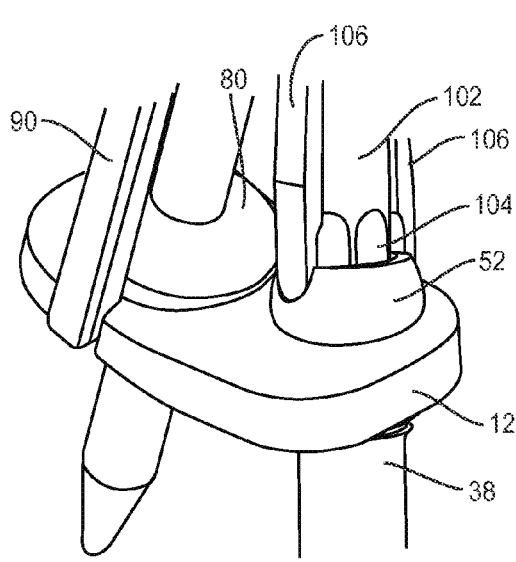
FIG. 8 is an enlarged view of the components shown in FIG. 7.
Figure 9:
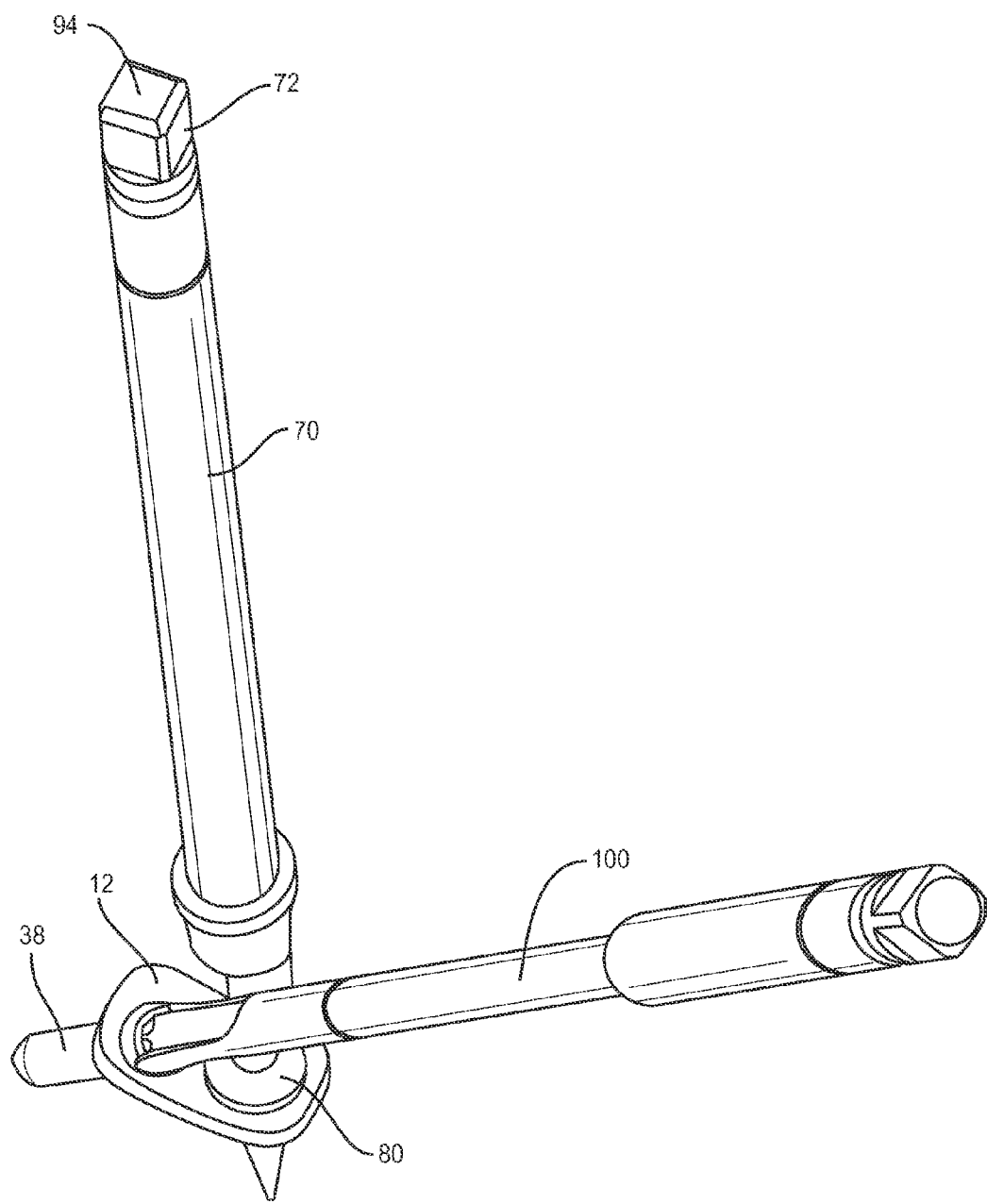
FIG. 9 is a perspective view of the components shown in FIG. 7.

Driver 100 is attached with nail 38. Prongs 106 are aligned with recesses 60 of nail 38. Portion 104 is engaged with portion 54. Prongs 106 translate over surface 58 into recesses 60 such that prongs 106 are deflected outward, as shown by arrow B in FIG. 6. Deflection of prongs 106 causes the resultant bias of prongs 106 to form a friction fit between surfaces 108 and surface 58 to releasably fix driver 100 with plate 12. Nail 38 is aligned and disposed with opening 36, as shown in FIG. 7, along an alar trajectory TA, as shown in FIG. 13, to penetrate tissue of an ala region A of sacrum S and facilitate engagement of nail 38 with region A.

Figure 12:
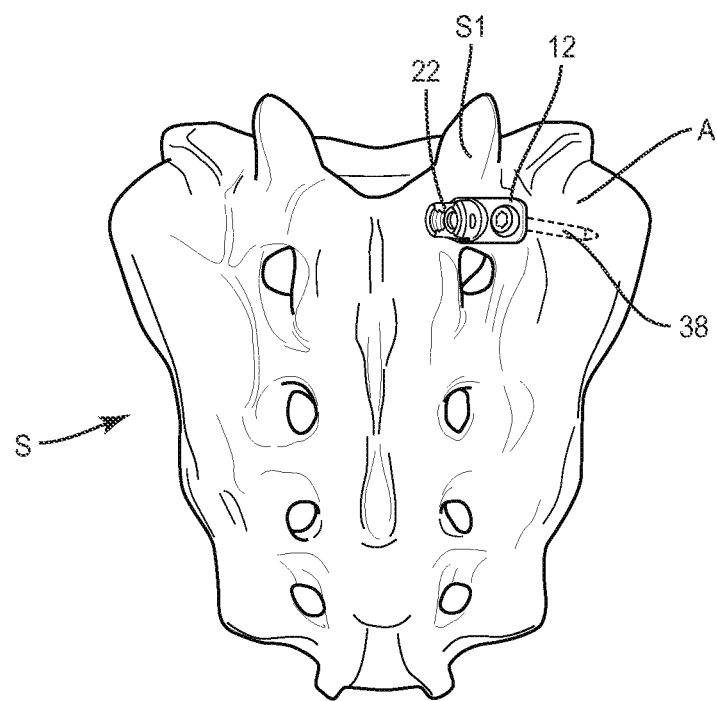
FIG. 12 is a plan view of components of one embodiment of a system in accordance with the principles of the present disclosure disposed with vertebrae.
Figure 13:
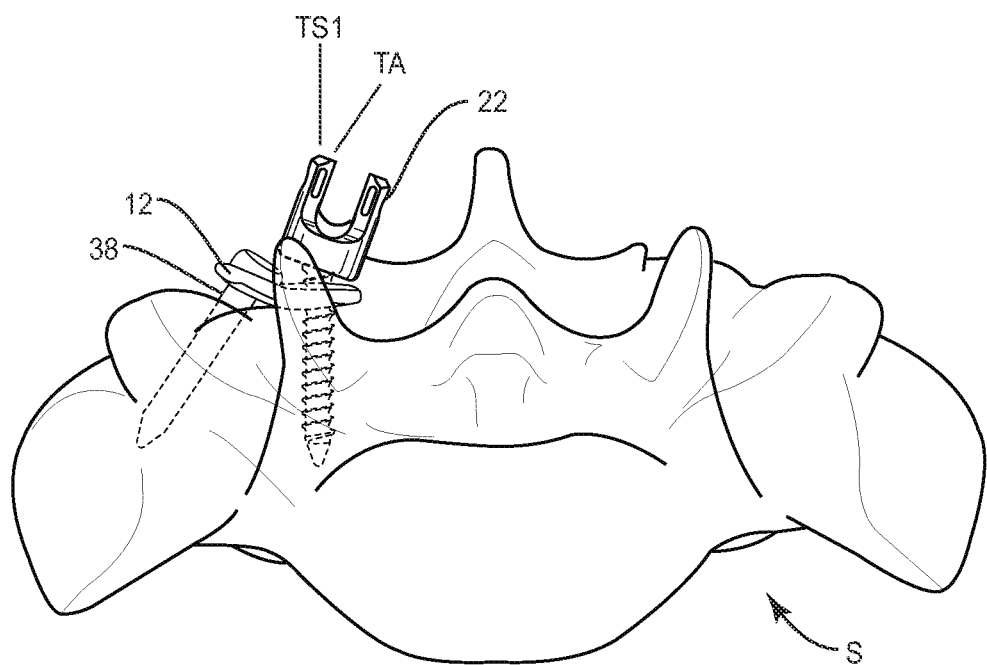
FIG. 13 is an axial view of components of one embodiment of a system in accordance with the principles of the present disclosure disposed with vertebrae.
Figure 14:
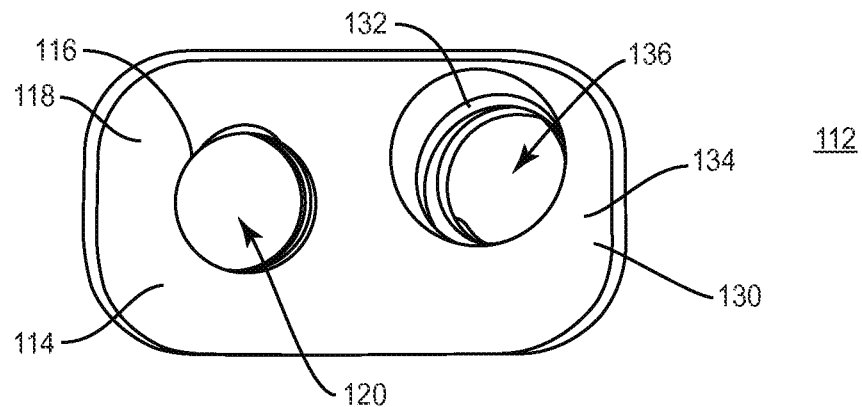
FIG. 14 is a top view of components of one embodiment of a system in accordance with the principles of the present disclosure.
Figure 15:
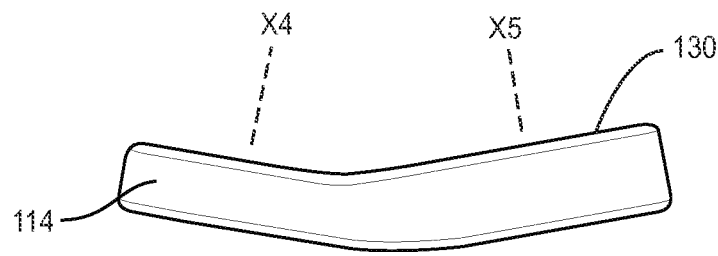
FIG. 15 is a side view of the components shown in FIG. 14.
Figure 16:
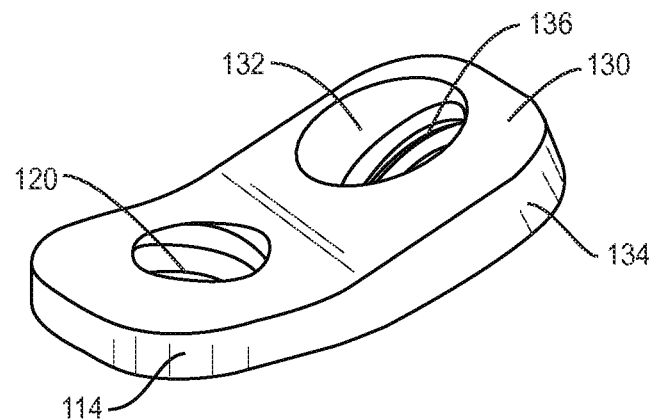
FIG. 16 is a perspective view of the components shown in FIG. 14.
Figure 17:
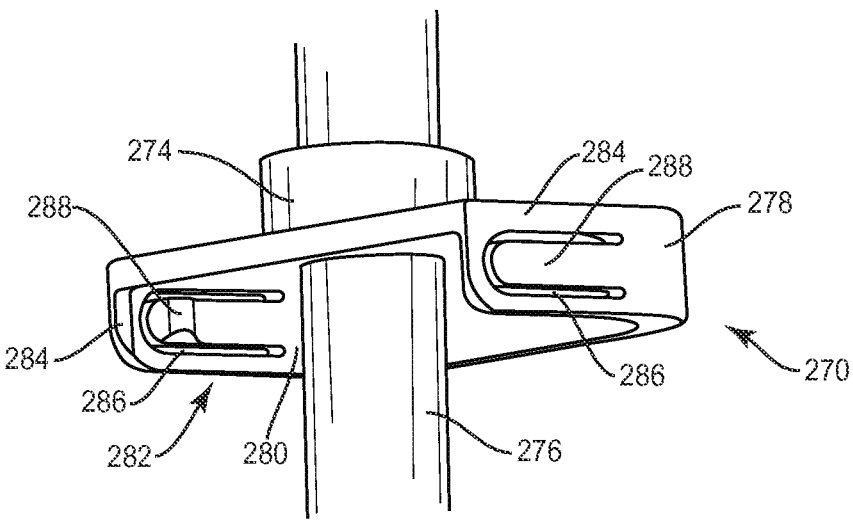
FIG. 17 is a perspective view of a component of one embodiment of a system in accordance with the principles of the present disclosure.
Figure 18:
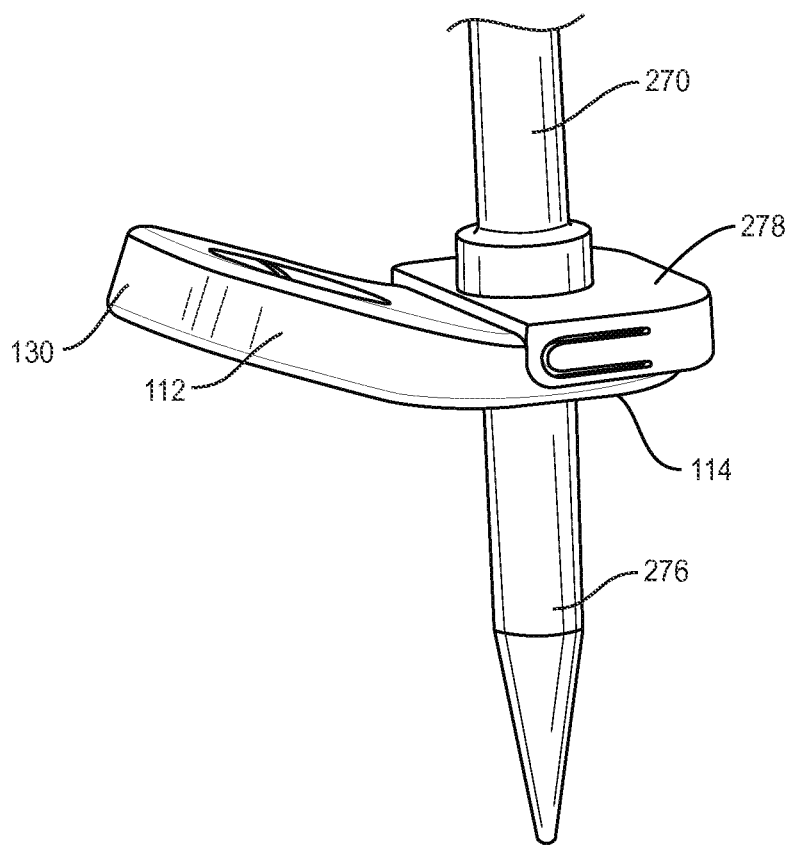
FIG. 18 is a break away view of components of one embodiment of a system in accordance with the principles of the present disclosure.
Figure 19:
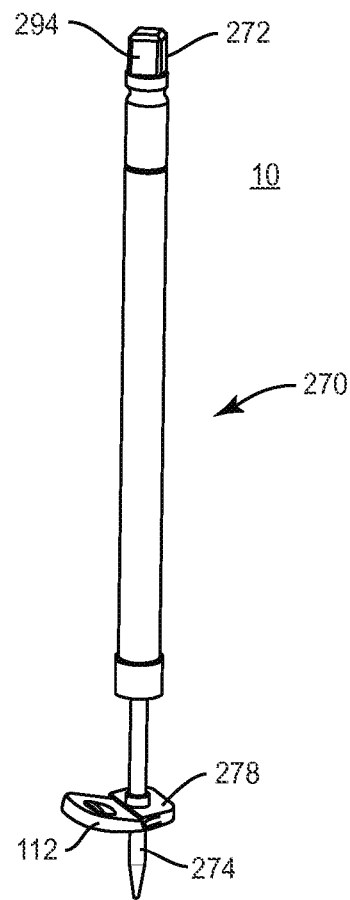
FIG. 19 is a perspective view of the components shown in FIG. 18.
Figure 20:
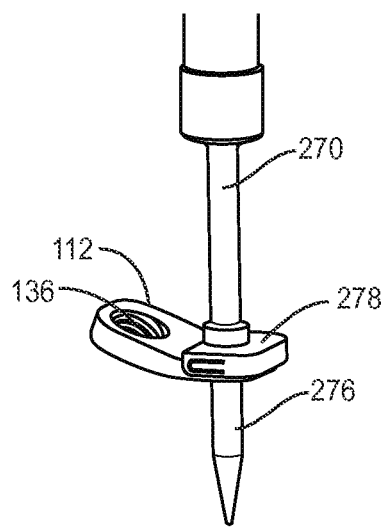
FIG. 20 is a break away view of the components shown in FIG. 18.

Awl 70 is removed and MAS 22 is engaged with opening 20 and the S1 vertebra of sacrum S in threaded fixation, as shown in FIGS. 12 and 13. In one embodiment, MAS 22 is disposed such that head 40 is positioned above and/or in engagement with head 52 of alar nail 38 to prevent back out of nail 38 from plate 12 by resisting, preventing and/or blocking axial translation of alar nail 38 through opening 36.

Upon completion of a procedure, as described herein, the surgical instruments, assemblies and non-implanted components of system 10 are removed and the incision(s) are closed. One or more of the components of system 10 can be made of radiolucent materials such as polymers. Radiomarkers may be included for identification under x-ray, fluoroscopy, CT or other imaging techniques. In some embodiments, the use of surgical navigation, microsurgical and image guided technologies may be employed to access, view and repair spinal deterioration or damage, with the aid of system 10. In some embodiments, system 10 may include one or a plurality of rods, plates, connectors and/or bone fasteners for use with a single vertebral level or a plurality of vertebral levels.

In some embodiments, one or more of fasteners may be engaged with tissue in various orientations, such as, for example, series, parallel, offset, staggered and/or alternate vertebral levels. In some embodiments, one or more of fasteners may comprise multi-axial screws, sagittal angulation screws, pedicle screws, mono-axial screws, uni-planar screws, facet screws, fixed axis screws, tissue penetrating screws, conventional screws, expanding screws, wedges, anchors, buttons, clips, snaps, friction fittings, compressive fittings, expanding rivets, staples, nails, adhesives, posts, fixation plates and/or posts.

In one embodiment, system 10 includes an agent, which may be disposed, packed, coated or layered within, on or about the components and/or surfaces of system 10. In some embodiments, the agent may include bone growth promoting material, such as, for example, bone graft to enhance fixation of the components and/or surfaces of system 10 with vertebrae. In some embodiments, the agent may include one or a plurality of therapeutic agents and/or pharmacological agents for release, including sustained release, to treat, for example, pain, inflammation and degeneration.

In one embodiment, as shown in FIGS. 15-24, system 10, similar to the systems and methods described herein, includes a medial-lateral plate 112, similar to plate 12, which can be employed with MAS 22, alar nail 38 and driver 100 as described herein. Plate 112 includes a wall 114 having an inner surface 116 and an outer surface 118, similar to surface 18 described herein.

Wall 114 defines an opening 120 configured to receive MAS 22. Opening 120 defines an axis X4. In some embodiments, opening 120 is aligned with a surgical pathway, approach and/or trajectory, as described herein, to orient MAS 22 for implantation with tissue, such as, for example, an S1 vertebra of a sacrum S, as described herein. In some embodiments, opening 120 is aligned with a surgical pathway, approach and/or trajectory that communicates with a posterior mid-line surgical pathway, approach and/or trajectory, as described herein. In some embodiments, opening 120 includes a threaded surface configured to facilitate engagement with a threaded shaft of MAS 22, as described herein.

Plate 112 includes a wall 130 including an inner surface 132 and an outer surface 134. Surface 132 defines an opening 136. Opening 136 defines an axis X5 and is configured to receive alar nail 38. Opening 136 is configured for disposal of alar nail 38 and aligns alar nail 38 with axis X5. As such, the longitudinal axis of alar nail 38 is co-axial with axis X5. In some embodiments, opening 136 may be threaded for engagement with alar screw 38.

In some embodiments, axis X5 is disposed at an angle relative to axis X4, similar to that described herein. In some embodiments, MAS 22 is aligned with axis X5 for implantation with an S1 vertebra and alar nail 38 is aligned with axis X5 for implantation with an alar region of a sacrum to attach plate 112 with a sacrum, as described herein.

In some embodiments, system 10 includes a surgical instrument, such as, for example, an awl 270, as shown in FIGS. 17-22. Awl 270 includes an end 272 and an end 274. End 274 includes a shaft 276 configured for penetrating tissue. Awl 270 is configured for disposal with wall 114 to provisionally fix placement of plate 112 at the surgical site and/or to form a pilot hole in a sacrum for MAS 22. Awl 270 includes an engagement portion, such as, for example, a plate 278.

Plate 278 includes a surface 280 that defines a cavity 282. Cavity 282 is configured for disposal of wall 114. Cavity 282 includes sidewalls 284. Sidewalls 284 each include a slot 286 and a spring tab 288. Spring tab 288 is biased to form a friction fit with wall 114 to releasably fix awl 270 with plate 112. As shaft 276 translates through opening 120, wall 114 engages sidewalls 284 and is disposed in cavity 282 such that tabs 288 deflect to form a friction fit with surface 118 of wall 114. In some embodiments, the engagement portion may have alternate cross section configurations, such as, for example, oval, oblong, triangular, square, polygonal, irregular, uniform, non-uniform, offset, staggered, and/or tapered to facilitate engagement with wall 114. In some embodiments, tab 288 includes a projection engageable with a detent or recess of plate 112.

End 272 includes a tool engaging portion 294 configured to engage a surgical tool or instrument, as described herein. In one embodiment, portion 294 includes a hexagonal cross-section to facilitate engagement with a surgical tool or instrument, as described herein.

Figure 21:
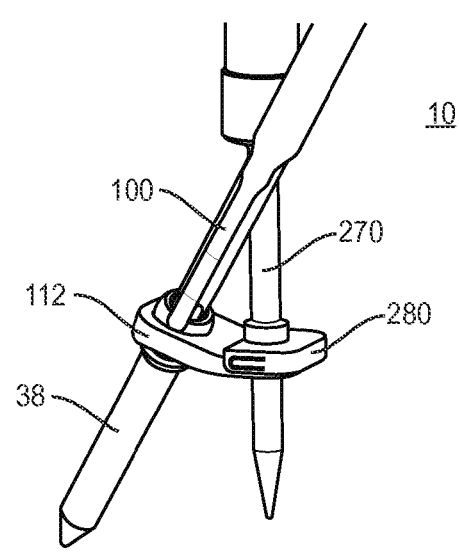
FIG. 21 is a break away view of components of one embodiment of a system in accordance with the principles of the present disclosure.

In use, similar to that described herein, as shown in FIGS. 18-24, awl 270 is connected with opening 120 of the selected plate 112. Shaft 276 is passed through opening 120 such wall 114 is disposed in cavity 282. Wall 114 is nested with walls 284 and cavity 282. Tabs 288 translate over surface 118 such that tabs 288 are deflected outward within slot 286. Deflection of tabs 288 causes a resultant bias of tabs 288 to form a friction fit between surface 118 and surface 280 to releasably fix awl 270 with plate 112. Plate 112 is delivered along a surgical pathway to the surgical site, similar to that described herein. Driver 100 is attached with nail 38, as shown in FIG. 21 and similar to that described herein, to penetrate tissue of an ala region.

Awl 270 is removed and MAS 22 is engaged with opening 120 and a sacrum in threaded fixation. In one embodiment, MAS 22 is disposed such that head 40 is positioned above and/or in engagement with head 52 of alar nail 38 to prevent back out of nail 38 from plate 112 by resisting, preventing and/or blocking axial translation of alar nail 38 through opening.

In one embodiment, as shown in FIGS. 25-30, system 10, similar to the systems and methods described herein, includes a medial-lateral plate 312, similar to plate 12, which can be employed with MAS 22, alar nail 38 and driver 100 as described herein. Plate 312 includes a wall 314 having an inner surface 316 and an outer surface 318, similar to surface 318 described herein.

Wall 314 defines an opening 320 configured to receive MAS 22. Opening 320 defines an axis X7. In some embodiments, opening 320 is aligned with a surgical pathway, approach and/or trajectory, as described herein, to orient MAS 22 for implantation with tissue of a sacrum S, as described herein.

Plate 312 includes a wall 330 including an inner surface 332 and an outer surface 334. Surface 332 defines an opening 336. Opening 336 defines an axis X8 and is configured to receive alar nail 38. Opening 336 is configured for disposal of alar nail 38 and aligns alar nail 38 with axis X8. As such, the longitudinal axis of alar nail 38 is co-axial with axis X8.

Figure 25:
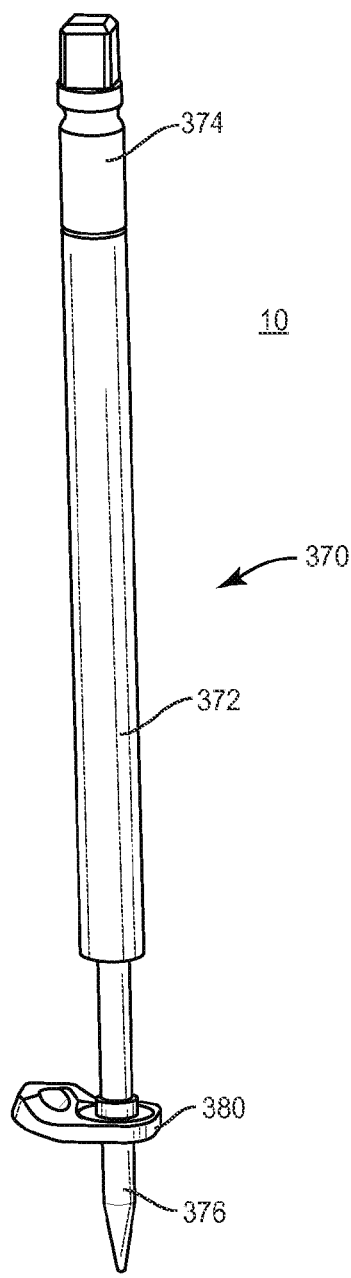
FIG. 25 is a perspective view of components of one embodiment of a system in accordance with the principles of the present disclosure.
Figure 26:
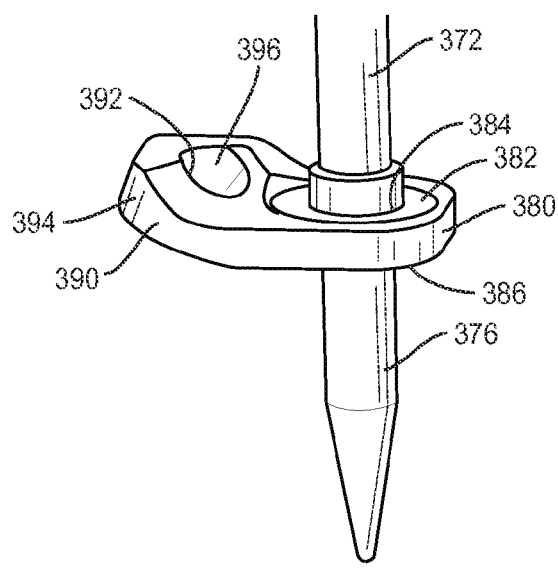
FIG. 26 is a break away view of the components shown in FIG. 25.

System 10 includes a surgical instrument, such as, for example, an awl guide 370, as shown in FIG. 25. Awl guide 370 includes a shaft 372 extending between an end 374 and an end 376. End 376 is configured for penetrating tissue. Shaft 372 includes a provisional plate 380 configured to align with openings 320, 336 of a selected plate 312 from one or a plurality of plates of a kit or system, similar to that described herein. In some embodiments, system 10 includes a plurality of awl guides 370 corresponding to the plurality of plates 312.

Provisional plate 380 includes a wall 382 having an inner surface 384 and an outer surface 386. In some embodiments, shaft 372 is monolithically formed with surface 384 such that shaft 372 is in alignment with axis X7 of plate 312 to form a cavity and/or pilot hole in the sacrum that is aligned with opening 320. Shaft 372 is rigidly connected with provisional plate 380 to form a rigid interface between awl guide 370 and plate 380 so that the trajectory of nail 38 is aligned with opening 336 of plate 312, as described herein.

Provisional plate 380 includes a wall 390 including an inner surface 392 and an outer surface 394. Surface 392 defines an opening 396. Opening 396 is oriented for alignment with axis X8 of plate 312 and is configured to receive a surgical tool, such as, for example, an alar nail awl 398. Opening 396 is in alignment with axis X8 of plate 312 such that awl 398 forms a cavity in the ala aligned with opening 336.

In use, similar to that described herein, a selected awl guide 370, as shown in FIG. 25, corresponding to a selected plate 312 for a particular treatment of vertebrae as determined by a medical practitioner from a plurality of plates of a kit of system 10, is introduced adjacent a surgical site, similar to that described herein. End 376 is aligned and engaged with a sacrum to penetrate tissue of an S1 vertebra of the sacrum to form a pilot hole in the S1 vertebra, similar to that described herein.

Figure 27:
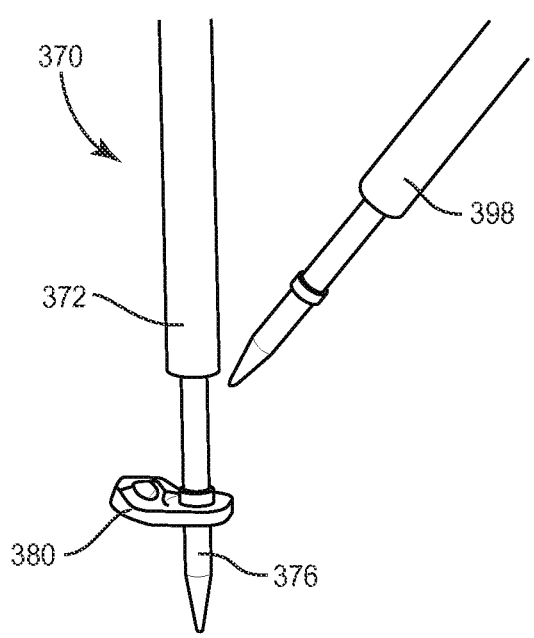
FIG. 27 is a break away view of components of one embodiment of a system in accordance with the principles of the present disclosure.

Surface 386 is engaged with the tissue of the S1 vertebra and surface 394 is engaged with tissue of the ala of the sacrum. Opening 396 is oriented for alignment with axis X8 of plate 312 and is configured to receive alar nail awl 398. Awl 398 is translated, as shown in FIG. 27, through opening 396 and forms a pilot hole in the ala for alignment with opening 336.

Figure 28:
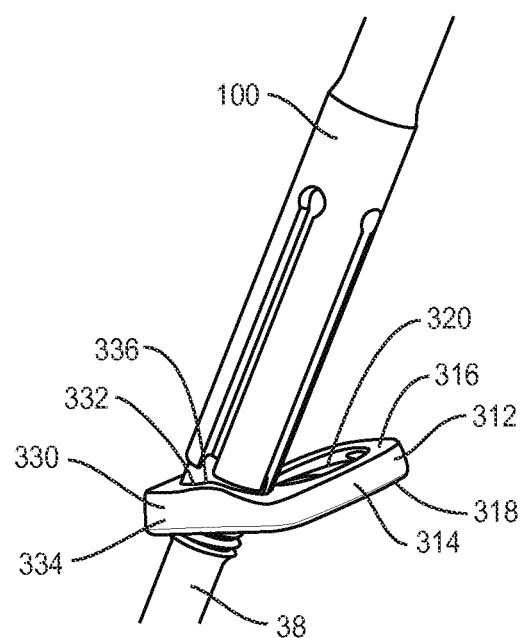
FIG. 28 is a break away view of components of one embodiment of a system in accordance with the principles of the present disclosure.
Figure 29:
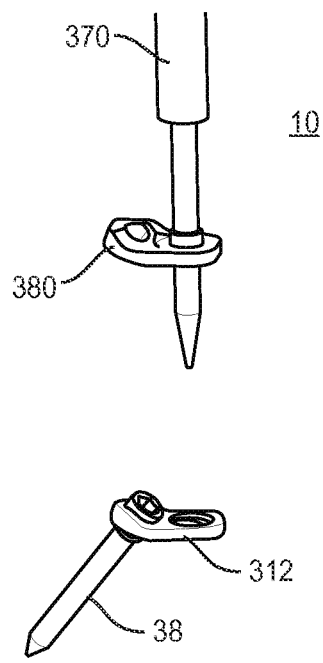
FIG. 29 is a break away view of components of one embodiment of a system in accordance with the principles of the present disclosure.

A length of nail 38 is determined by the medical practitioner. Nail 38 is connected with driver 100, as shown in FIG. 28, similar to that described herein, and plate 312, similar to that described herein, in an assembly of plate 312 and nail 38. Awl guide 370 is removed from the surgical site, as shown in FIG. 29. The plate 312/nail 38 assembly is introduced and/or delivered adjacent the surgical site and nail 38 is aligned with the pilot hole created by awl 398 and engaged with the tissue of the alar for fixation therewith.

Figure 30:
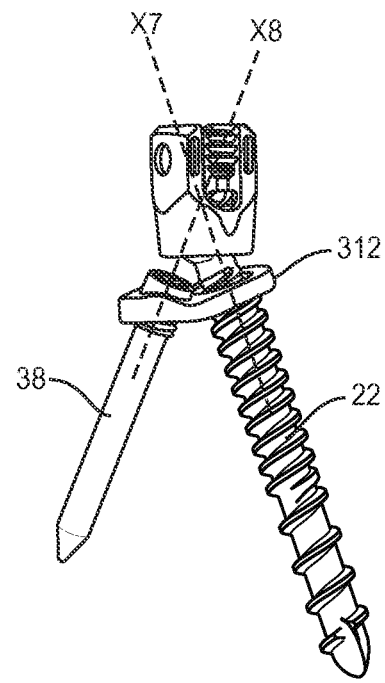
FIG. 30 is a perspective view of components of one embodiment of a system in accordance with the principles of the present disclosure.

Plate 312 is engaged with the tissue of the sacrum, similar to that described herein, such that opening 320 is aligned with the pilot hole formed by end 376 in the tissue of the S1 vertebra. MAS 22 is engaged with plate 312, as shown in FIG. 30.

Figure 31:
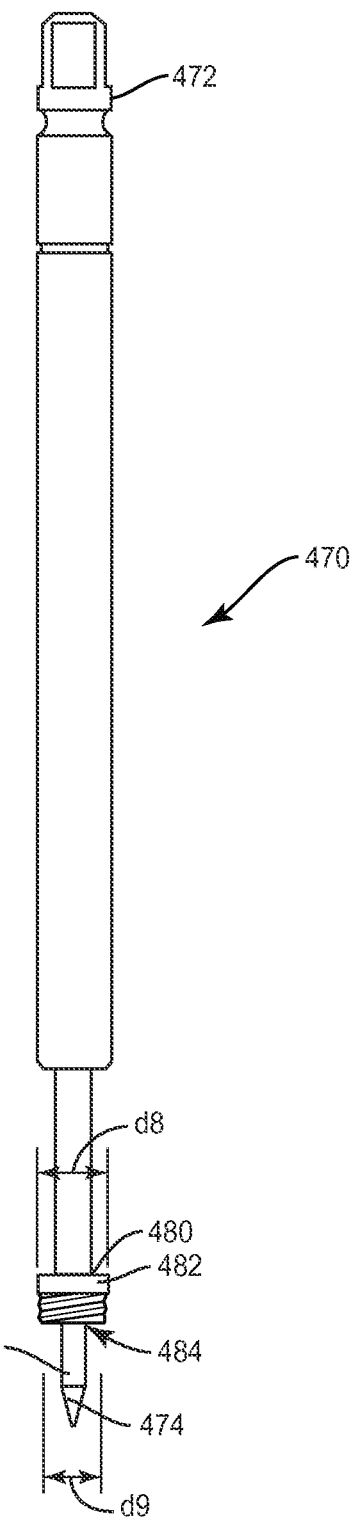
FIG. 31 is a side view of components of one embodiment of a system in accordance with the principles of the present disclosure.
Figure 32:
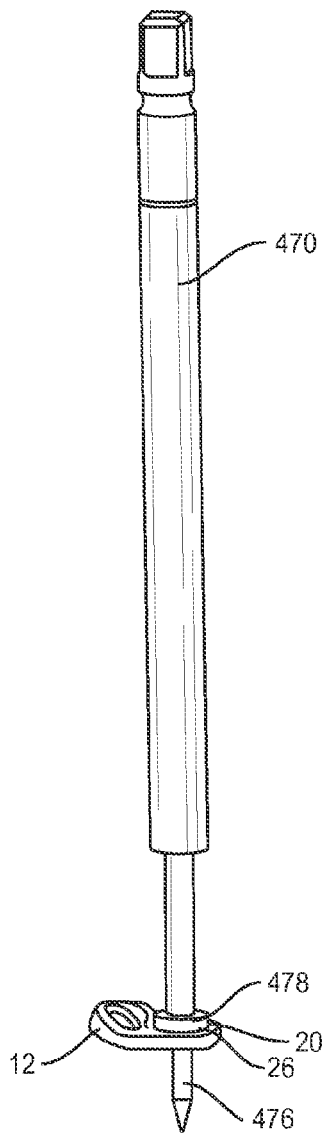
FIG. 32 is a perspective view of components of one embodiment of a system in accordance with the principles of the present disclosure.
Figure 33:
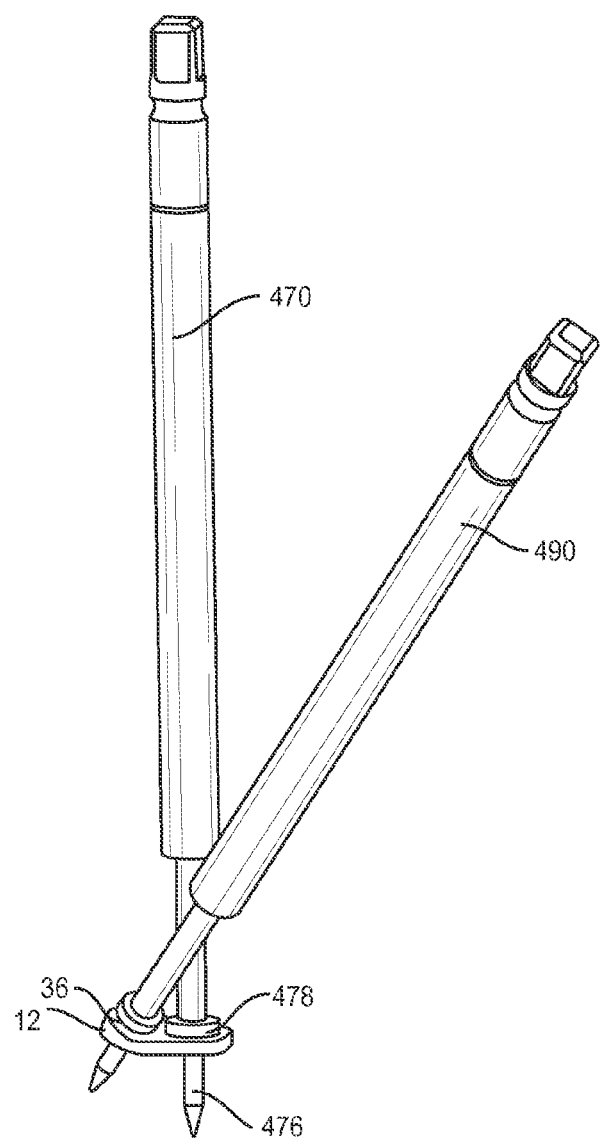
FIG. 33 is a perspective view of components of one embodiment of a system in accordance with the principles of the present disclosure.

In one embodiment, as shown in FIGS. 31-37, system 10, similar to the systems and methods described herein, includes a surgical instrument, such as, for example, an awl 470. Awl 470 includes an end 472 and an end 474. End 474 includes a shaft 476 configured for penetrating tissue. Awl 470 is configured for disposal with opening 20 to provisionally fix placement of plate 12 at the surgical site and/or to form a pilot hole in an S1 vertebra of a sacrum for MAS 22, similar to that described herein. Awl 470 includes an engagement portion, such as, for example, a disc 478 configured for engagement with pocket 26, as described herein. Disc 478 includes a surface 480 that defines a wall 482. Wall 482 is configured for nesting engagement with wall 27 (FIG. 5). Disc 478 includes a diameter d8. Awl 470 includes a threaded surface 484 disposed adjacent disc 478. In one embodiment, as shown in FIG. 31, surface 484 is disposed distal to disc 478. Surface 484 includes a diameter d9. Diameter d9 is less than diameter d8 such that surface 484 is engageable with opening 20 such that disc 478 nests in pocket 26.

In use, similar to that described herein, awl 470, as shown in FIG. 31, is introduced adjacent a surgical site, similar to that described herein. Awl 470 is engaged with plate 12 by rotating awl 470 such that surface 484 engages opening 20 causing disc 478 to nest with pocket 26 in threaded fixation. In one embodiment, an alar awl 490, similar to that described herein, is disposed for engagement with opening 36 of plate 12.

Figure 34:
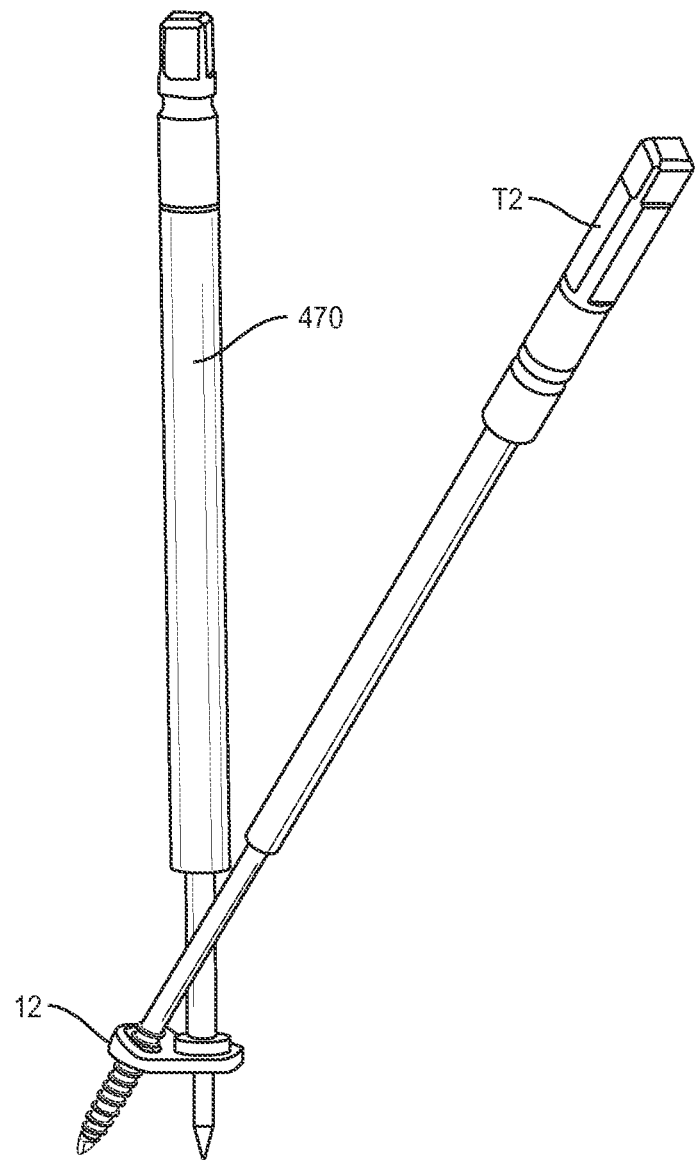
FIG. 34 is a perspective view of components of one embodiment of a system in accordance with the principles of the present disclosure.
Figure 37:
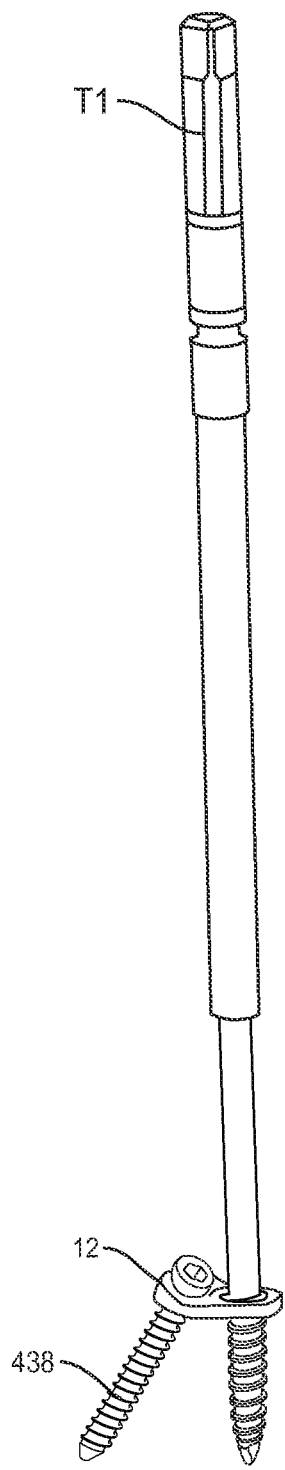
FIG. 37 is a perspective view of components of one embodiment of a system in accordance with the principles of the present disclosure.

Awl 490 is removed and a tap T2, as shown in FIG. 34, is utilized to form a pilot hole with the tissue of a region along the alar trajectory TA, similar to that described herein with regard to FIG. 13. Awl 470 is removed and a tap T1, as shown in FIG. 37 is oriented to form a pilot hole with the tissue of sacrum S along the S1 trajectory in the S1 vertebra, similar to that described herein with regard to FIG. 13.

Figure 35:
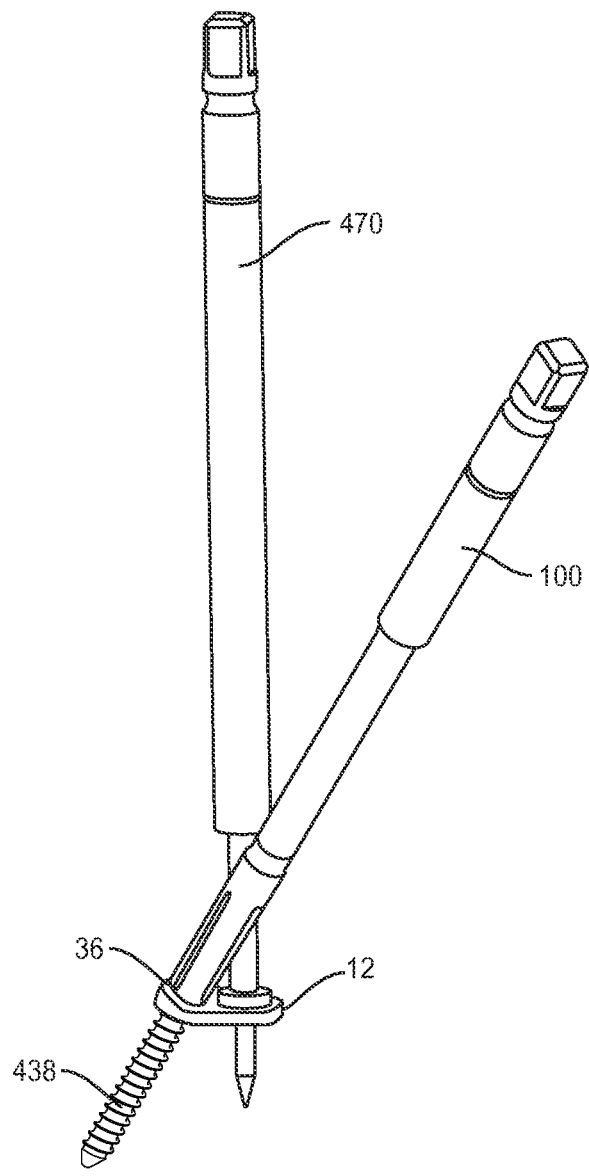
FIG. 35 is a perspective view of components of one embodiment of a system in accordance with the principles of the present disclosure.
Figure 36:
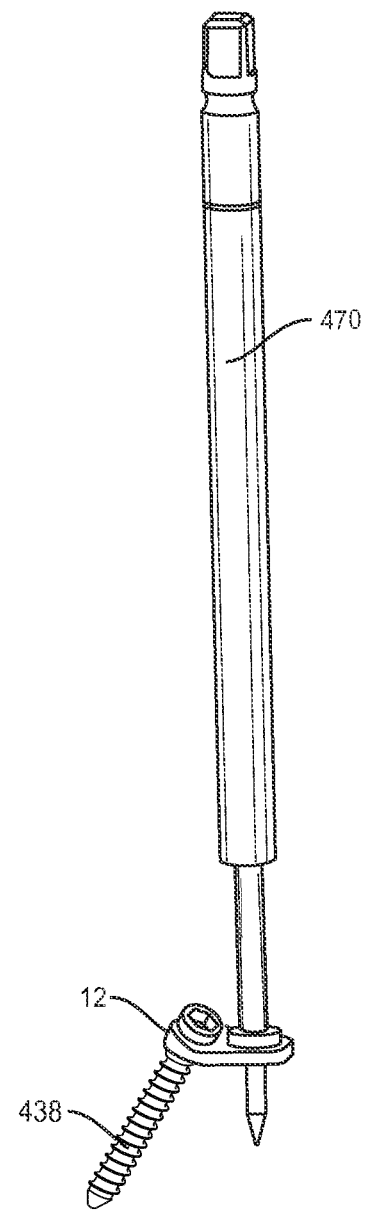
FIG. 36 is a perspective view of components of one embodiment of a system in accordance with the principles of the present disclosure.

Driver 100 is attached with screw 438, as described herein. Screw 438 is aligned and disposed with opening 36, as shown in FIG. 35, along the alar trajectory TA, to penetrate tissue of an ala region of the sacrum and facilitate engagement of screw 438. MAS 22 is engaged with plate 12 and tissue of the sacrum S, similar to that described herein with regard to FIG. 13, in connected with a selected treatment, similar to those described herein.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. A spinal implant system comprising:
 a plate including opposite top and bottom surfaces that define a thickness of the plate, the plate comprising a first cavity oriented to implant a multi-axial fastener with a sacrum and a second cavity oriented to implant a fastener with an ala of the sacrum, the plate comprising a pocket that surrounds the first cavity, the pocket extending into the top surface without extending through the bottom surface; and
 a surgical instrument engageable with the plate, the surgical instrument comprising a handle and a shaft that extends from the handle, the shaft including a pointed tip, the surgical instrument comprising a disc between the handle and the tip and a threaded surface between the disc and the tip,
 wherein the surgical instrument is configured for disposal in the first cavity such that the disc nests in the pocket.

2. The spinal implant system as recited in claim 1, wherein the surgical instrument comprises an awl.

3. The spinal implant system as recited in claim 1, wherein each of the cavities are configured for alignment with a pathway that communicates with a posterior mid-line surgical approach.

4. The spinal implant system as recited in claim 1, wherein the first cavity is oriented to implant the multi-axial fastener with an S1 vertebra of the sacrum.

5. The spinal implant system as recited in claim 1, wherein the multi-axial fastener engages the fastener to prevent translation of the fastener relative to the plate.

6. The spinal implant system as recited in claim 1, wherein the disc has a maximum diameter that is greater than a maximum diameter of the threaded surface.

7. The spinal implant system as recited in claim 1, wherein the shaft includes a first end that is connected to the shaft and an opposite second end, the second end including a tool engaging portion configured to engage a surgical tool.

8. The spinal implant system as recited in claim 1, wherein the shaft includes a first end that is connected to the shaft and an opposite second end, the second end including a tool engaging portion configured to engage a surgical tool, the tool engaging portion having a hexagonal cross-section to facilitate engagement with a surgical tool or instrument.

9. The spinal implant system as recited in claim 1, wherein the shaft has a maximum diameter that is less than a maximum diameter of the disc and a maximum diameter of the threaded portion.

10. The spinal implant system as recited in claim 1, wherein the shaft is coaxial with the disc and the threaded portion.

11. The spinal implant system as recited in claim 1, wherein the surgical instrument is free of threads from the threaded portion to the tip.

12. The spinal implant system as recited in claim 1, further comprising an alar awl positioned in the second cavity.

13. A spinal implant system comprising:
 a plate including a first wall having opposite top and bottom surfaces that define a thickness of the first wall, the plate including a second wall having opposite top and bottom surfaces that define a thickness of the second wall, the plate comprising a first cavity that extends through the first wall and a second cavity that extends through the second wall, the plate comprising a pocket that surrounds the first cavity, the pocket extending into the top surface of the first wall without extending through the bottom surface of the first wall; and a surgical instrument engageable with the plate, the surgical instrument comprising a handle and a shaft that extends from the handle, the shaft including a pointed tip, the surgical instrument comprising a disc between the handle and the tip and a threaded surface between the disc and the tip, wherein the surgical instrument is configured for disposal in the first cavity such that the disc nests in the pocket.

14. The spinal implant system as recited in claim 13, wherein the first cavity defines a first axis that extends perpendicular to the top and bottom surfaces of the first wall and the second cavity defines a second axis that perpendicular to the top and bottom surfaces of the second wall, the first axis extending at an acute angle relative to the second axis.

15. The spinal implant system as recited in claim 14, wherein the acute angle is about 20 degrees.

16. The spinal implant system as recited in claim 14, wherein the acute angle is about 45 degrees.

17. The spinal implant system as recited in claim 13, wherein the disc has a maximum diameter that is greater than a maximum diameter of the threaded surface.

18. The spinal implant system as recited in claim 13, wherein the shaft includes a first end that is connected to the shaft and an opposite second end, the second end including a tool engaging portion configured to engage a surgical tool, the tool engaging portion having a hexagonal cross-section to facilitate engagement with a surgical tool or instrument.

19. The spinal implant system as recited in claim 13, wherein the shaft has a maximum diameter that is less than a maximum diameter of the disc and a maximum diameter of the threaded portion.

20. The spinal implant system as recited in claim 13, wherein the shaft is coaxial with the disc and the threaded portion.

21. The spinal implant system as recited in claim 13, wherein the surgical instrument is free of threads from the threaded portion to the tip.

22. The spinal implant system as recited in claim 13, further comprising an alar awl positioned in the second cavity.

* * * * *

UNITED STATES PATENT AND TRADEMARK OFFICE
CERTIFICATE OF CORRECTION

PATENT NO. : 10,172,650 B2  
APPLICATION NO. : 14/520100  
DATED : January 8, 2019  
INVENTOR(S) : Hynes et al.

It is certified that error appears in the above-identified patent and that said Letters Patent is hereby corrected as shown below:

In the Specification

In Column 1, Line 14, delete "hemiation," and insert -- herniation, --, therefor.

In Column 6, Line 23, delete "dearly" and insert -- clearly --, therefor.

In Column 11, Line 66, delete "Shaft 74" and insert -- Shaft 76 --, therefor.

In Column 11, Line 67, delete "disc 80" and insert -- disc 78 --, therefor.

In Column 12, Line 52, delete "dips," and insert -- clips, --, therefor.

Signed and Sealed this  
Eighth Day of October, 2019

Andrei Iancu  
*Director of the United States Patent and Trademark Office*